United States Patent [19]

Unroe et al.

[11] Patent Number: 4,667,002
[45] Date of Patent: May 19, 1987

[54] PHENYLQUINOXALINE RESIN COMPOSITIONS

[75] Inventors: Marilyn R. Unroe, Dayton; Bruce A. Reinhardt, New Carlisle; Fred E. Arnold, Centerville, all of Ohio

[73] Assignee: The United States of America as represented by the Secretary of the Air Force, Washington, D.C.

[21] Appl. No.: 819,322

[22] Filed: Jan. 16, 1986

[51] Int. Cl.$^4$ ............................................. C08F 26/06
[52] U.S. Cl. ..................................... 526/259; 544/353
[58] Field of Search ......................... 526/259; 544/353

[56] References Cited

U.S. PATENT DOCUMENTS

| | | | |
|---|---|---|---|
| 3,852,244 | 12/1974 | Heath | 260/50 |
| 3,966,729 | 6/1976 | Kovar et al. | 260/250 Q |
| 4,147,868 | 4/1979 | Arnold et al. | 544/353 |
| 4,375,536 | 3/1983 | Hergenrother | 528/125 |

Primary Examiner—Paul R. Michl
Assistant Examiner—Alex H. Walker
Attorney, Agent, or Firm—Charles E. Bricker; Donald J. Singer

[57] ABSTRACT

Phenylquinoxaline monomers containing sterically hindered ethynyl groups are provided. These monomers can be crosslinked to provide thermoset resins of the general formula

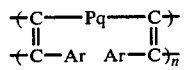

wherein Pq is a phenylquinoxaline linking unit. Ar is an aromatic ether or thioether, and n has a value between 2 and 3.

5 Claims, No Drawings

4,667,002

PHENYLQUINOXALINE RESIN COMPOSITIONS

RIGHTS OF THE GOVERNMENT

The invention described herein may be manufactured and used by or for the Government of the United States for all governmental purposes without the payment of any royalty.

BACKGROUND OF THE INVENTION

This invention relates to phenylquinoxaline resin compositions.

The acetylene-terminated polyphenylquinoxalines disclosed in U.S. Pat. Nos. 3,966,729 and 4,147,868 represent promising new matrix resins for advanced structural materials. These materials propagate and cure by addition reactions to form high molecular weight, thermally stable compositions. The addition process obviates all problems associated with volatile by-product formation that occurs when such materials are prepared by condensation processes.

The thermally induced free radical polymerization of aromatic and heterocyclic diacetylenes provides a linear conjugated polyene of 6 to 8 repeating units which results in a cluster-shaped species whose growth is inhibited by the steric hindrance of the monomer or oligomer backbone structure. Although the free radical at the hub of the cluster is reactive its growth becomes increasingly more difficult as the reaction proceeds, reaching a finite limit. Subsequent reaction of dangling acetylene groups of a cluster results in a highly cross-linked polyene network. Such cross-linking has a direct effect on the network topology which manifests itself in mechanical behavior.

It is an object of the present invention to provide novel quinoxaline resin systems having a low crosslink density.

Other objects and advantages of the present invention will be apparent to those skilled in the art.

SUMMARY OF THE INVENTION

In accordance with the present invention there is provided a phenylquinoxaline polyene of the general formula $$\begin{array}{c}(\!\!\!\begin{array}{cc}C\!\!-\!\!-\!\!-Pq\!\!-\!\!-\!\!-C\\ \|\ \ \ \ \ \ \ \ \ \ \ \ \ \ \ \ \ \|\\ C\!\!-\!\!Ar\ \ Ar\!\!-\!\!C\end{array}\!\!\!)_n\end{array} \quad \text{I}$$

wherein n has a value of about 2 to 3; wherein Pq has the general formula

[structure shown]

wherein X is a single bond, $-O-$, $-S-$, $-SO_2-$, $-CH_2-$, $-CO-$, $-OC_6H_4O-$, $-O-C_6H_4-C_6H_4-O-$, $-O-C_{10}H_6-O-$ or $-O-C_6H_4-SO_2-C_6H_4-O-$ and wherein Ar has the general formula

[structure shown]

wherein m has a value of 1 or 2, Z is $-O-$ or $-S-$, and Q is $-H$, $-ZC_6H_5$ or $-SO_2C_6H_5$.

The polyene (formula I) is prepared by the thermally induced free radical polymerization of the bulky secondary acetylene-containing quinoxaline monomer (II) having the general formula $$Ar-C\equiv C-Pq-C\equiv C-Ar \quad \text{II}$$

wherein Pq and Ar are as defined previously.

The monomer (II) is prepared by the reaction of a suitable benzil (III) containing an aryloxyethynyl moiety with a suitable aromatic tetraamine (IV). The reaction involved can be represented by the following equation in which the Roman numerals refer to the compositions indicated in the previous sentence.

[structure III shown]

[structure IV shown] $\longrightarrow$ II

In the foregoing equation, Ar and X are as indicated previously.

The aromatic bis(o-diamines) (IV) are well known compounds that are described in the literature. Examples of suitable bis(o-diamines) include 3,3′,4,4′-tetraaminobiphenyl; 3,3′,4,4′-tetraaminodiphenylether; 3,3′,4,4′-tetraaminodiphenylsulfide; 3,3′,4,4′-tetraaminodiphenylsulfone; 3,3′,4,4′-diphenylmethane; 3,3′,4,4′-tetraaminozbenzophenone, 1,3-bis(3,4-diaminophenoxy)-benzene, 2,2′-bis(3,4-diaminophenoxy)-biphenyl; 1,5-bis(3,4-diaminophenoxy)naphthalene; 4,4′-bis(3,4-diaminophenoxy)-diphenylsulfone; and the like.

The benzils (III) can be prepared by reacting an acetylene-terminated aromatic ether of the general formula Ar—C≡CH, wherein Ar is as described previously, with a halophenoxy benzil of the general formula

[structure shown]

wherein Y is $-Cl$ or $-Br$, in the presence of a catalytic amount of a catalyst system consisting of a substituted phosphine, a complex palladium salt containing two halogen moieties and two substituted phosphine moieties, and a cuprous halide. The substituted phosphine may have substituents selected from the group consisting of C1 to C4 alkyl and C1 to C4 alkyl-substituted phenyl. Suitable phosphines include triphenylphosphine, triethylphosphine, diphenylethylphosphine, and the like. In the complex palladium salt the halogen can be —I, —Cl or —Br, and the substituted phosphine is as just described. The cuprous halide may be the bromide, iodide or chloride.

The acetylene-terminated aromatic ether and the halophenoxy benzil are reacted using an excess of the ether, generally about 1.5X to 3X.

The catalyst system described above is employed in an amount ranging from about 1 to about 10 weight percent of the total weight of the reactants. In the catalyst system the relative amounts of the Pd complex salt, the substituted phosphine and the cuprous halide can range from about 1:1:1 to 20:25:1, respectively.

The reaction of the benzil with the ether can be carried out under relatively mild conditions, including a temperature in the approximate range of 20° to 200° C., preferably about 50° to 125° C. Normal reaction pressure is atmospheric, although increased reaction pressure of up to about 250 psig can be employed. Reaction time is somewhat dependent upon the particular charge stock and catalyst system and the reaction temperature. In general, the reaction time can be from 1 to 150 hours, but more usually about 3 to 24 hours.

The above reaction is carried out in the presence of a suitable basic solvent, preferably an amine solvent. Suitable solvents include diamethylamine, trimethylamine, diethylamine, triethylamine, ethylpropylamine, ethylbutylamine, dibutylamine and the like.

Preparation of the monomer (II) is carried out by contacting the benzil (III) with the tetraamine (IV) under an inert atmosphere, such as nitrogen, in a suitable solvent, such as DMF, in the presence of a catalytic amount of a lower alkyl carboxylic acid. The amount of catalyst used can vary within rather wide limits, but usually ranges from about 0.5 to 10 volume percent of the solvent. Generally, stoichiometric amounts of the reactants will be employed. The reaction temperature can range from about 0° C. to about 100° C. and reaction time generally ranges from 1 to 50 hours.

The crude monomer can be recovered by pouring the reaction mixture into an excess of precipitating solvent, such as water. The monomer can be purified using techniques known in the art.

The monomers of this invention can be heat cured to provide thermoset resins. When heated to temperatures on the order of 300° C., the monomers undergo intramolecular crosslinking to form the polyene I. The polyene (I) is then cured, in air or under an inert atmosphere such as nitrogen at a temperature in the approximate range of 300°–400° C. for about 1 to 50 hours.

When used as a coating material, the products of the invention should be laid down on the substrate and heat cured at temperatures of 300° C. or higher. To prepare laminates, the fabric may be impregnated with a solvent solution of the polymer, e.g., n-hexane, then rinsed with a non-solvent for the polymer, e.g., methanol, to precipitate the polymer in the interstices of the fabric and to remove the solvent. The dried fabric can then be laid up and heated to cross-link the resin solids. Modest pressures on the order of 15–200 psig are sufficient, if employed. Curing temperatures on the order of 300°–350° C. are employed for curing times on the order of about 1 to 24 hours. The laminates may be post cured for 10 to 50 hours at temperatures of about 300°–350° C. Alternatively, the laminate fabric may be dusted with dry resin powder, instead of the solvent procedure described above.

The following examples illustrate the invention:

EXAMPLE I

Preparation of 4-(3-bromophenoxy)benzil

To a 250 ml flask fitted with reflux condenser, thermometer, and nitrogen inlet were added 4-nitrobenzil (10.83 g, 42.49 mmol), 3-bromophenol (7.35 g, 42.49 mmol) and dimethylsulfoxide (150 ml). After stirring at room temperature for 20 minutes under a nitrogen atmosphere, potassium carbonate (11.73 g, 84.98 mmol) was added to the flask and the flask was heated to an internal temperature of 95° C. for 19 h under nitrogen. When cooled to room temperature the solution was very slowly poured into 12N HCL(500 ml) and extracted with methylene chloride (2×100 ml). The organic layer was washed with water (3×500 ml), dried over anhydrous magnesium sulfate, and evaporated to dryness by rotary evaporation. The light orange oil was then dissolved in 4:1 hexane:methylene chloride and chromatographed on a silica gel column (Woelm DCC, 211.94 g, 5 cm dia×24 cm H). The purified product was recrystallized twice from methylene chloride:methanol (25 ml:150 ml) to afford light yellow crystals (11.08 g, 69%): mp 75°–76° C.

Analysis Cacl'd for $C_{20}H_{13}O_3Br$: C, 63.16; H, 3.42; Br, 20.96. Found: C, 62.90, H, 3.47; Br, 20.57.

EXAMPLE II

Preparation of 4-[m-[[m-(m-phenoxyphenoxy)phenyl]ethynyl]phenoxy]benzil

To a 250 ml flask fitted with a reflux condenser, nitrogen inlet and thermometer were added 4(3-bromophenoxy)benzil (11.08 g, 29.08 mmol), 1-(3-ethynylphenoxy)-3-phenoxybenzene (21.64 g, 75.66 mmol), triethylamine (150 ml), and triphenylphosphine (0.40 g). After stirring at room temperature under a nitrogen atmosphere for 10 minutes, cuprous iodide (Alfa 98%, 0.20 g) and dichlorobis (triphenylphosphine) palladium (II) (0.20 g) were added. The flask was heated to an internal temperature of 90° C. and maintained by oil bath heating under nitrogen until TLC indicated reaction completion (4 hr). The triethylamine was distilled from the residue and the residue was suspended in toluene. The toluene was washed with 15% HCl (560 ml) twice and separated. The organic layer was washed with ethylenediamine (20 ml) by adding the ethylenediamine at room temperature, heating to 60° C. for 0.5 h and cooling. Water (250 ml) was added and the toluene was separated from the aqueous layer. The ethylenediamine wash was repeated once more. After washing with water (3×500 ml), the organic layer was dried over anhydrous magnesium sulfate (3.00 g) and the toluene distilled by rotary evaporation at reduced pressure to give a dark brown oil. The oil was dissolved in 4:1 hexane:methylene chloride and chromatographed on a silica gel column (Woelm DCC, 230 g, 5 cm dia×25 cm H) using 4:1 hexane:methylene chloride as the eluent. The product was dried in a 70° C. oven under reduced pressure to afford a light brown tacky oil (7.52 g, 44%).

EXAMPLE III

Preparation of
3,3'-Bis[p-[m-[[m-(m-phenoxyphenoxy)phenyl]ethynyl]phenoxy]phenyl]-2,2'-diphenyl-6,6'biquinoxaline To a 250 ml flask fitted with a nitrogen inlet-outlet were added the benzil of Example II (5.18 g, 8.84 mmol) and tetrahydrofuran(THF) (100 ml). After stirring for 10 minutes at room temperature under a nitrogen atmosphere 3,3'-diaminobenzidine was added (0.95 g, 4.42 mmol). After partial dissolving of the tetraamine (5 min), a catalytic quantity of glacial acetic acid (2 ml) was added. The solution was stirred at temperature under nitrogen for 20 h. The flask contents were poured into water (200 ml) and extracted with methylene chloride (2×100 ml). The organic layer was washed with 5% sodium carbonate (200 ml), water (3×200 ml), and dried over anhydrous magnesium-sulfate (6.00 g). The solvent was distilled by rotary evaporation to afford a dark yellow oil. The crude product was dissolved in 1:1 hexane: methylene chloride and chromatographed on a silica gel column (Woelm DCC, 124 g, 3 cm dia×34 cm H) using 1:1 hexane:methylene chloride to remove the impurities and 2:1 methylene chloride:hexane to remove the product. The product was precipitated twice from THF:methanol (10 ml/120 ml) and dried in a 60° C. oven under reduced pressure to afford a pale yellow powder (3.20 g, 38%).

Analysis calc'd for $C_{92}H_{58}O_6N_4$: C, 84.02; H, 4.41; N, 4.26. Found: C, 84.71; H, 4.64; N, 4.01.

EXAMPLE IV

A series of monomers was prepared generally following the procedure given in Example III. With reference to the monomer formula

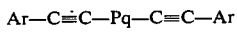

wherein Ar and Pq are as previously defined, this series had Ar groups identified as follows:

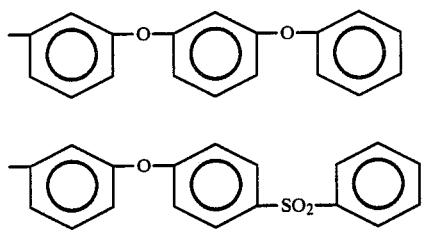

and bond —X— in the group Pq as shown in the Table below.

The glass transition temperatures of these monomers are set forth in the following Table. The glass transition temperature (second order transition temperature) was measured using a Differential Scanning Calorimeter (DuPont 990 Thermal Analyzer) at range 25°–450° C. with a scan speed of 20° C./min. Tg-cured was recorded after curing specimens under nitrogen for 24 hours at 312° C. (except as noted).

TABLE

| X | Ar | Tg-Init (°C.) | Tpoly Onset (°C.) | Tpoly Peak (°C.) | Tg-cured (°C.) |
|---|---|---|---|---|---|
| single bond | Ar (1) | 75 | 346 | 400 | 193 |
| single bond | Ar (2) | 124 | 353 | 399 | 242 |
| —O— | Ar (1) | 72 | 333 | 405 | 159 |
| —O— | Ar (2) | 122 | 350 | 402 | 223* |

*Cured under nitrogen for 48 hours at 312° C.

EXAMPLE V

For comparison, a monomer having the formula H—C≡C—Pq—C≡—H, wherein Pq is as previously defined, and wherein X in the group Pq is a single bond, was prepared, cross-linked by heating, and cured. The fracture toughness of the cured polymer was determined to be 0.59 Kq(MPa·√m). In contrast, the fracture toughness of the cured polymer is set forth in Example IV, wherein X is a single bond and wherein the Ar group is Ar(1), was determined to be 0.81 Kq(MPa·√m).

Various modifications and alterations may be made in the present invention without departing from the spirit thereof or the scope of the appended claims.

We claim:

1. A phenylquinoxaline polyene having repeating units of the general formula

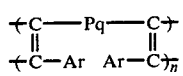

wherein n is about 2 to 3; wherein Pq has the general formula

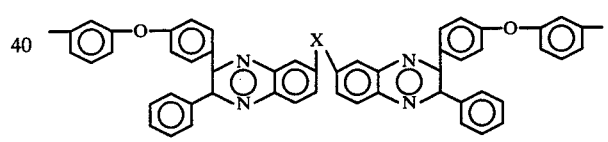

wherein X is a single bond, —O—, —S—, —SO₂—; —CH₂, —CO—, —OC₆H₄O—, —OC₆H₄—C₆H₄O—, —OC₁₀H₆O— or —OC₆H₄SO₂C₆H₄O—; and wherein Ar is

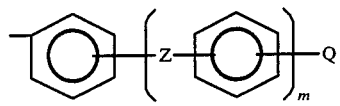

wherein m is an integer having a value of 1 or 2, Z is —O— or —S—, and Q is —H, —ZC₆H₅ or —SO₂C₆H₅.

2. The polyene of claim 1 wherein X is a single bond and Ar is

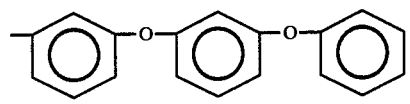

3. The polyene of claim 1 wherein X is —O— and Ar is

4. The polyene of claim 1 wherein X is a single bond and Ar is
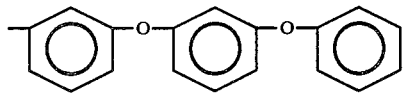
5. The polyene of claim 1 wherein X is —O— and Ar is
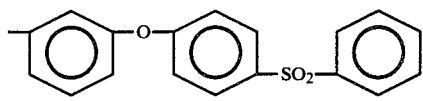
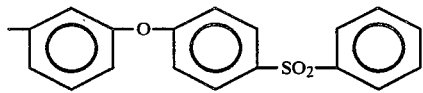
* * * * *